(12) United States Patent
Jungong et al.

(10) Patent No.: US 10,125,066 B1
(45) Date of Patent: Nov. 13, 2018

(54) PROCESS FOR MAKING HIGH PURITY 2-CHLORO-1,1,1,2-TETRAFLUOROPROPANE (HCFC-244BB)

(71) Applicant: Honeywell International Inc., Morris Plains, NJ (US)

(72) Inventors: Christian Jungong, Depew, NY (US); Daniel C. Merkel, Orchard Park, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/825,334

(22) Filed: Nov. 29, 2017

(51) Int. Cl.
| | |
|---|---|
| *C07C 17/087* | (2006.01) |
| *C07C 19/10* | (2006.01) |
| *C07C 21/18* | (2006.01) |
| *C07C 17/38* | (2006.01) |
| *C07C 17/25* | (2006.01) |
| *C07C 21/04* | (2006.01) |
| *B01J 23/44* | (2006.01) |
| *B01J 21/02* | (2006.01) |

(52) U.S. Cl.
CPC ............. *C07C 17/087* (2013.01); *B01J 21/02* (2013.01); *B01J 23/44* (2013.01); *C07C 17/25* (2013.01); *C07C 17/38* (2013.01); *C07C 19/10* (2013.01); *C07C 21/04* (2013.01); *C07C 21/18* (2013.01)

(58) Field of Classification Search
CPC ..... C07C 17/25; C07C 17/383; C07C 17/395; C07C 21/18; C07C 19/10; B01D 3/009; B01D 3/10; B01D 11/04; B01J 23/44
See application file for complete search history.

(56) References Cited

U.S. PATENT DOCUMENTS

| | | |
|---|---|---|
| 8,058,486 B2 | 11/2011 | Merkel et al. |
| 8,766,020 B2 | 7/2014 | Wang et al. |
| 8,975,454 B2 | 3/2015 | Merkel et al. |
| 2012/0065437 A1* | 3/2012 | Merkel .................... B01J 27/10 570/175 |

* cited by examiner

*Primary Examiner* — Jafar F Parsa
(74) *Attorney, Agent, or Firm* — Faegre Baker Daniels LLP

(57) ABSTRACT

A method for producing 2-chloro-1,1,1,2-tetrafluoropropane (HCFC-244bb) from a reaction composition including a mixture of HCFC-244bb and 2-chloro-3,3,3-trifluoropropene (HCFO-1233xf) by selectively hydrogenating the HCFO-1233xf component of the mixture in a vapor phase in the presence of hydrogen gas and a catalyst to generate a product composition including unreacted HCFC-244bb and hydrogenation products of HCFO-1233xf, such as 2-chloro-1,1,1-trifluoropropane (HCFC-253db), which may be separated from the HCFC-244bb by distillation. The separated HCFC-244bb may then be purified by subsequent acid neutralization and drying steps.

19 Claims, 1 Drawing Sheet

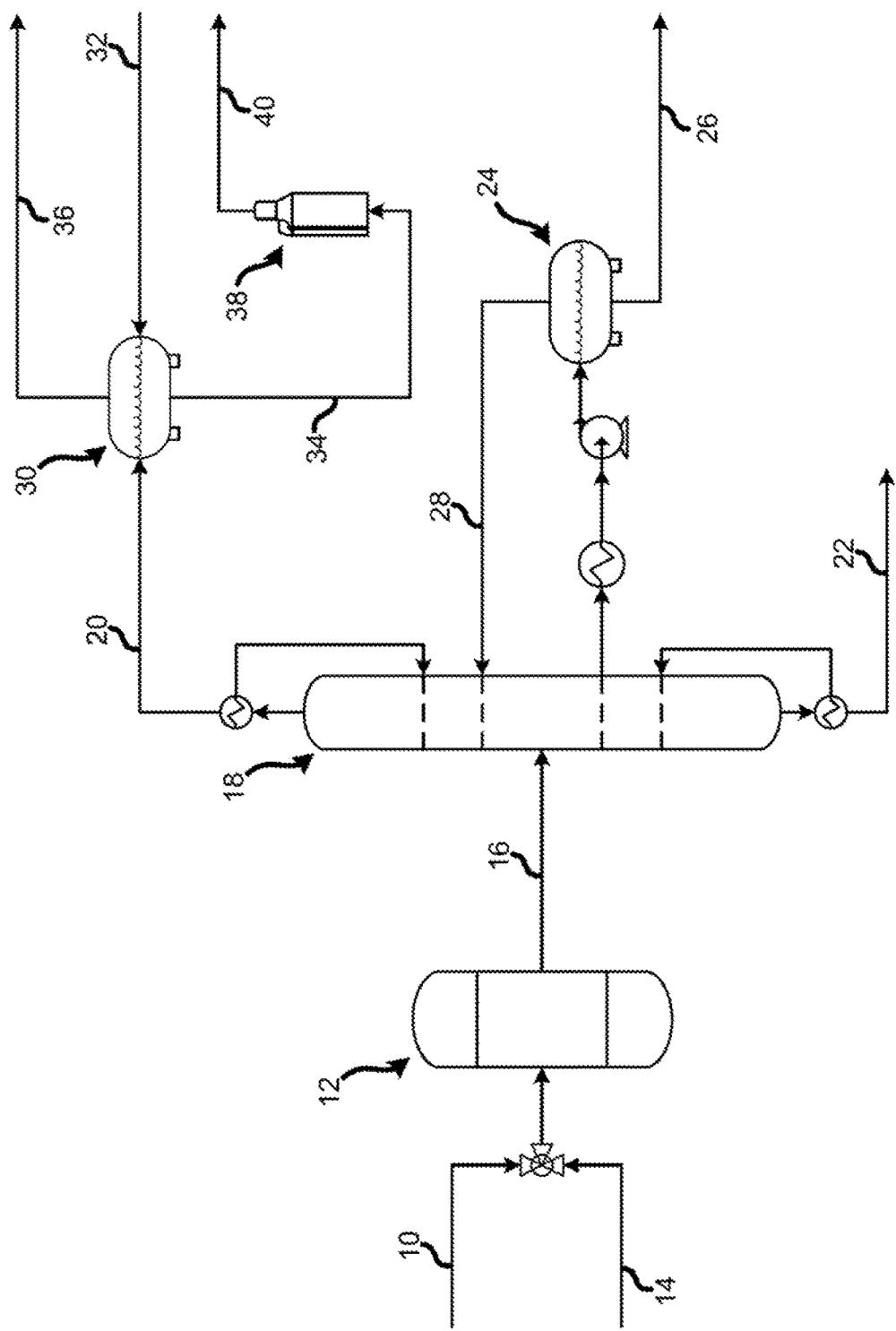

PROCESS FOR MAKING HIGH PURITY 2-CHLORO-1,1,1,2-TETRAFLUOROPROPANE (HCFC-244BB)

BACKGROUND

1. Field of the Disclosure

The present disclosure relates to a process for making high purity 2-chloro-1,1,1,2-tetrafluoropropane (HCFC-244bb, or 244bb).

2. Description of the Related Art

Hydrofluoroolefins (HFOs), such as tetrafluoropropenes are known as effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Due to suspected environmental problems associated with the use of some of these fluids, including the relatively high global warming potentials associated therewith, it is desirable to use fluids having the lowest possible global warming potential (GWP) in addition to also having zero ozone depletion potential (ODP). Thus, there is considerable interest in developing environmentally friendlier materials for the applications mentioned above.

Hydrofluoroolefins (HFOs) having zero ozone depletion and low global warming potential have been identified as potentially filling this need. However, the toxicity, boiling point, and other physical properties of these chemicals vary greatly from isomer to isomer. One HFO having valuable properties is 2,3,3,3-tetrafluoropropene (HFO-1234yf or 1234yf).

HFO-1234yf has been shown to be a low global warming compound with low toxicity and, thus, can meet increasingly stringent requirements for refrigerants in mobile air conditioning. Accordingly, compositions containing HFO-1234yf are among the materials being developed for use in many of the aforementioned applications.

Various methods are known for producing HFO-1234yf, such as those described in U.S. Pat. No. 8,058,486, entitled INTEGRATED PROCESS TO REPRODUCE 2,3,3,3-TETRAFLUOROPROPENE, issued on Nov. 15, 2011, U.S. Pat. No. 8,975,454, entitled PROCESS FOR PRODUCING 2,3,3,3-TETRAFLUOROPROPENE, issued on Mar. 10, 2015, and U.S. Pat. No. 8,766,020, entitled PROCESS FOR PRODUCING 2,3,3,3-TETRAFLUOROPROPENE issued on Jul. 1, 2014, all of which are herein incorporated by reference in their entirety.

2-chloro-1,1,1,2-tetrafluoropropane (HCFC-244bb, or 244bb) is an important intermediate in the manufacture of 2,3,3,3-tetrafluoropropene (HFO-1234yf, or 1234yf) which, in one exemplary application, is an environmentally benign replacement for 1,1,1,2-tetrafluoroethane (HFC-134a or 134a) in automobile air conditioners. As the automotive industry makes the transition from HFC-134a to HFO-1234yf, demand for HFO-1234yf has increased, and is paralleled by demand for robust, economical and environmentally benign processes for making HFO-1234yf.

The burgeoning interest in HFO-1234yf has resulted in several manufacturing processes that have been introduced for its production. One exemplary process is a multistep process including the step of hydrofluorination of 2-chloro-3,3,3-trifluoropropene (HCFO-1233xf, or 1233xf) with hydrogen fluoride (HF) to form HCFC-244bb. In a subsequent step, the HCFC-244bb is dehydrohalogenated to form HFO-1234yf.

However, HCFO-1233xf and HCFC244bb have similar boiling points, and corresponding mixtures of these compounds may exhibit azeotrope-like properties, making them inseparable by conventional distillation. In this manner, any formation of azeotrope-like mixtures of HCFO-1233xf and HCFC-244bb may lead to yield losses. Therefore, it is desired to separate the HCFO-1233xf and HCFC244bb intermediates during the manufacturing process to limit the amount of recycle, which translates to an increase in both capital and manufacturing cost.

Additionally, in the dehydrohalogenation step to make HFO-1234yf, a purified stream of HCFC-244bb may be desired for optimum catalyst stability as well as product selectivity, yield, and purity. Therefore, there is need to develop processes that can effectively separate mixtures of HCFO-1233xf and HCFC-244bb to produce HCFC-244bb of high purity.

SUMMARY

The present disclosure provides a method for producing 2-chloro-1,1,1,2-tetrafluoropropane (HCFC-244bb) from a reaction composition including a mixture of HCFC-244bb and 2-chloro-3,3,3-trifluoropropene (HCFO-1233xf) by selectively hydrogenating the HCFO-1233xf component of the mixture in a vapor phase in the presence of hydrogen gas and a catalyst to generate a product composition including unreacted HCFC-244bb and hydrogenation products of HCFO-1233xf, such as 2-chloro-1,1,1-trifluoropropane (HCFC-253db), which may be separated from the HCFC-244bb by distillation. The separated HCFC-244bb may then be purified by subsequent acid neutralization and drying steps.

In one form thereof, the present disclosure provides a method for producing 2-chloro-1,1,1,2-tetrafluoropropane (HCFC-244bb), including the steps of: providing a reactant stream including a mixture of HCFC-244bb and 2-chloro-3,3,3-trifluoropropene (HCFO-1233xf); and hydrogenating the HCFO-1233xf of the reactant stream in a vapor phase in the presence of hydrogen gas and a catalyst to generate a product composition including unreacted HCFC-244bb and 2-chloro-1,1,1-trifluoropropane (HCFC-253db).

In one embodiment, the catalyst of the hydrogenation step is a palladium catalyst. The palladium catalyst may be supported on an alumina support, the catalyst including between 0.3 wt. % and 5 wt. %, based on the total weight of the palladium catalyst and the aluminum support.

The reactant stream may include between 75 wt. % and 98 wt. % HCFC-244bb, based on the total weight of the reactant stream. The reactant stream may include between 1 wt. % and 25 wt. % HCFO-1233xf, based on the total weight of the reactant stream.

The hydrogenation step may further include hydrogenating at a temperature between 100° C. and 250° C. The hydrogenation step may further include hydrogenating at a pressure between 5 psig and 100 psig.

The method may include the additional step of separating the HCFC-244bb and the HCFC-253db. The method may further include the additional steps of: subjecting the separated HCFC-244bb to an acid neutralization step; and drying the acid neutralized HCFC-244bb, Following the drying step, the HCFC-244bb may have at least one of: a purity greater than 95 wt. %; a water content less than 10 ppm; and an acid content less than 1 ppm.

In the hydrogenating step, conversion of HCFO-1233xf may exceed 98% and/or selectivity of HCFO-1233xf to HCFC-253db exceeds 60%.

In another form thereof, the present disclosure provides a method for producing 2-chloro-1,1,1,2-tetrafluoropropane (HCFC-244bb), including the steps of: providing a reactant stream including a mixture of HCFC-244bb and 2-chloro-3,3,3-trifluoropropene (HCFO-1233xf); hydrogenating the HCFO-1233xf of the reactant stream in a vapor phase in the presence of hydrogen gas and a palladium metal catalyst at a temperature between 100° C. and 250° C. to generate a product composition including unreacted HCFC-244bb and 2-chloro-1,1,1-trifluoropropane (HCFC-253db); and separating the HCFC-244bb and the HCFC-253db.

The method may further include the additional steps of: subjecting the separated HCFC-244bb to an acid neutralization step; and drying the acid neutralized HCFC-244bb. Following the drying step, the HCFC-244bb may have a purity greater than 95 wt. %, a water content less than 10 ppm, and an acid content less than 1 ppm.

The palladium catalyst may be supported on an alumina support, the catalyst including between 0.3 wt. % and 5 wt. %, based on the total weight of the palladium catalyst and the aluminum support.

The reactant stream may include between 75 wt. % and 98 wt. % HCFC-244bb, based on the total weight of the reactant stream, and/or the reactant stream may include between 1 wt. % and 25 wt. % HCFO-1233xf, based on the total weight of the reactant stream.

The hydrogenation step may further include hydrogenating at a pressure between 5 psig and 100 psig. In the hydrogenating step, conversion of HCFO-1233xf may exceed 98%.

BRIEF DESCRIPTION OF THE DRAWINGS

The above mentioned and other features of the disclosure, and the manner of attaining them, will become more apparent and the disclosure itself will be better understood by reference to the following description of embodiments of the disclosure taken in conjunction with the accompanying drawings.

FIG. 1 is a process diagram schematically illustrating an exemplary process according to the present disclosure for producing high purity HCFC-244bb.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates an embodiment of the disclosure, and such exemplification is not to be construed as limiting the scope of the disclosure in any manner.

DETAILED DESCRIPTION

The present disclosure provides a method for producing 2-chloro-1,1,1,2-tetrafluoropropane (HCFC-244bb) from a reaction composition including a mixture of HCFC-244bb and 2-chloro-3,3,3-trifluoropropene (HCFO-1233xf) by selectively hydrogenating the HCFO-1233xf component of the mixture in a vapor phase in the presence of hydrogen gas and a catalyst to generate a product composition including unreacted HCFC-244bb and hydrogenation products of HCFO-1233xf, such as 2-chloro-1,1,1-trifluoropropane (HCFC-253db), which may be separated from the HCFC-244bb by distillation. The separated HCFC-244bb may then be purified by subsequent acid neutralization and drying steps.

As briefly described above, this disclosure provides a purified HCFC-244bb composition that is suitable for the manufacture of 2,3,3,3-tetrafluoropropene (HFO-1234yf, or 1234yf). The manufacture of HCFC-244bb from 2-chloro-3,3,3-trifluoropropene (HCFO-1233xf) and hydrogen fluoride (HF), with subsequent conversion of HCFC-244bb to HFO-1234yf, can be generalized in a three step process, described below.

Step 1 of this process involves the production of 2-chloro-3,3,3-trifluoropropene (HCFO-1233xf) from 1,1,2,3-tetrachloropropene (HCC-1230xa, or 1230xa) in a vapor phase reactor according to the following reaction scheme:

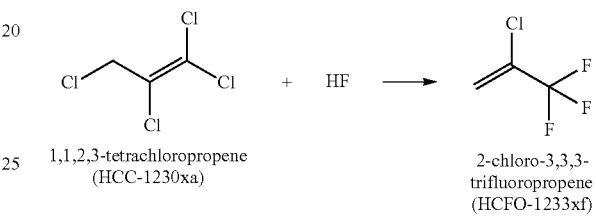

1,1,2,3-tetrachloropropene
(HCC-1230xa)

2-chloro-3,3,3-
trifluoropropene
(HCFO-1233xf)

Step 2 of this process involves the production of 2-chloro-1,1,1,2-tetrafluoropropane (HCFC-244bb) from 2-chloro-3,3,3-trifluoropropene (HCFO-1233xf) in a reactor, such as a liquid phase reactor, according to the following reaction scheme:

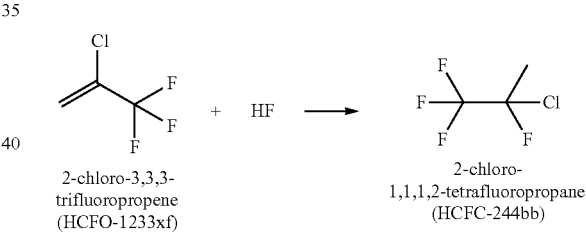

2-chloro-3,3,3-
trifluoropropene
(HCFO-1233xf)

2-chloro-
1,1,1,2-tetrafluoropropane
(HCFC-244bb)

Step 3 of this process involves the production of 2,3,3,3-tetrafluoropropene (HFO-1234yf) from 2-chloro-1,1,1,2-tetrafluoropropane (HCFC-244bb) in a reactor, such as a vapor phase reactor according to the following reaction scheme:

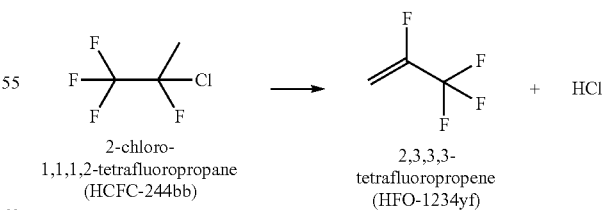

2-chloro-
1,1,1,2-tetrafluoropropane
(HCFC-244bb)

2,3,3,3-
tetrafluoropropene
(HFO-1234yf)

The present disclosure presents an integrated process to make high purity HCFC-244bb from mixtures of HCFO-1233xf and HCFC-244bb, generally including the steps of: (a) selective reaction of HCFO-1233xf, (b) separation of attendant by-products from HCFC-244bb, and (c) acid neutralization and drying of HCFC-244bb.

According to the present process, the step of selective reaction of HCFO-1233xf utilizes the reactivity of HCFO-1233xf to selectively convert HCFO-1233xf to form by-products that are readily separable from HCFC-244bb, such as by conventional distillation. In particular, according to the present process, a mixture of HCFO-1233xf and HCFC-244bb is subjected to a hydrogenation reaction in the vapor phase in the presence of hydrogen gas and a hydrogenation catalyst that selectively favors the hydrogenation of HCFO-1233xf with little or no significant reaction of HCFC-244bb. In this manner, HCFC-244bb may remain an essentially non-reactive, or "spectator", compound during the selective hydrogenation of HCFO-1233xf.

The hydrogenation of HCFO-1233xf in the vapor phase, using hydrogen gas, over a hydrogenation catalyst results in the formation of by-products, including 2-chloro-1,1,1-trifluoropropane (HCFC-253db or 253db). HCFC-253db has a higher boiling point relative to HCFO-1233xf and HCFC-244bb and does not form azeotropic compositions with either HCFO-1233xf or HCFC-244bb, such that HCFC-253db may be readily separated from any remaining unreacted HCFO-1233xf and from the HCFC-244bb by conventional distillation. Also, the HCFC-253db formed in this reaction is itself a value—added intermediate and has applications as a precursor for making monomers and other refrigerants.

Referring to FIG. 1, a reactant stream 10 including a mixture of HCFO-1233xf or HCFC-244bb is fed to reactor 12. In one embodiment, the reactant stream 10 includes a relatively greater relative amount of HCFC-244bb and a relatively lesser amount of HCFO-1233xf. Also, a stream 14 of hydrogen gas is combined into stream 10 upstream of reactor 12 as shown, or alternatively, stream 14 may be separately fed to reactor 12.

For example, the amount of HCFC-244bb in the reactant stream 10 may be as little as 75 wt. %, 80 wt. % or 85 wt. %, or as great as 90 wt. %, 95 wt. %, 99.9 wt. %, or may be within any range defined between any pair of the foregoing values, such as 75 wt. % to 99.9 wt. %, 80 wt. % to 95 wt. %, or 85 wt. % to 90 wt. %, based on the total weight of the reactant stream.

The amount of HCFO-1233xf in the reactant stream 10 may be as little as 0.1 wt. %, 1 wt. %, 2 wt. %, or 5 wt. %, or as great as 10 wt. %, 15 wt. %, 25 wt. %, or may be within any range defined between any pair of the foregoing values, such as 0.1 wt. % to 25 wt. %, 1 wt. % to 15 wt. %, or 5 wt. % to 10 wt. %, for example, based on the total weight of the reactant stream.

The reactant stream 10 may also include relatively minor amounts of impurities, i.e., compounds other than HCFC-244bb, HCFO-1233xf, and hydrogen, typically in an amount of less than 1.5 wt. %, less than 1.0 wt. %, or 0.5 wt. %. The foregoing amounts in the preceding two paragraphs are exclusive of the amount of hydrogen gas which is supplied to the reactor 12.

A stream of hydrogen gas 14 is also supplied to reactor 12 and, in the reactor 12, the mole ratio of hydrogen gas to HCFO-1233xf is between 1.2 and 1.7:1, or between 1.3 and 1.6:1, for example.

In reactor 12, the mixture of HCFO-1233xf and HCFC-244bb is subjected to a hydrogenation reaction in the vapor phase in the presence of the hydrogen gas and a hydrogenation catalyst, described in further detail below.

Due to the fact that HCFO-1233xf is more susceptible towards hydrogenation than HCFC-244bb, when the mixture is subjected to hydrogenation conditions in the reactor, the hydrogenation catalyst and hydrogen gas may be used undiluted. Additionally, the reduced concentration of HCFO-1233xf in the reactant stream of HCFO-1233xf and HCFC-244bb limits the heat generation and occurrence of exotherms in the reactor during the hydrogenation of HCFO-1233xf.

However, in view of the fact that hydrogenations performed in the gas phase are exothermic, to assure better thermal management one or more of the following techniques may be applied.

First, as discussed in further detail below, the hydrogenation catalyst may be diluted in an inert support.

Second, the reactant stream that is supplied to the reactor may be diluted by an inert diluent. Suitable inert diluents include helium, argon, saturated hydrocarbons, and saturated fluorocarbons. The diluent(s) are present in the reaction mixture in an amount as little as 2 wt. %, 5 wt. %, or 10 wt. %, or as great as 15 wt. %, 20 wt. %, or 25 wt. %, or within any range defined between any two of the foregoing values, such as 2 to 25 wt. %, 5 to 20 wt. %, or 10 to 15 wt. %, for example, based on the total weight of the HCFO-1233xf and HCFC-244bb in reactant stream 10 supplied to reactor 12.

Third, the hydrogen gas that is supplied to the reactor may be diluted by an inert diluent. Suitable inert diluents include helium, argon, saturated hydrocarbons, and saturated fluorocarbons. The diluent(s) are present in the hydrogen gas in an amount as little as 2 wt. %, 5 wt. %, or 10 wt. %, or as great as 20 wt. %, 30 wt. %, or 40 wt. %, or within any range defined between any two of the foregoing values, such as 2 to 40 wt. %, 5 to 30 wt. %, or 10 to 20 wt. %, for example, based on the total weight of the hydrogen gas in stream 14 supplied to reactor 12.

The catalyst used to selectively hydrogenate HCFO-1233xf from a mixture of HCFO-1233xf and HCFC-244bb in the gas phase to form HCFC-253db may be palladium metal on alumina support ($Pd/Al_2O_3$). The wt. % of palladium metal on the alumina support amount as little as 0.3 wt. %, 0.5 wt. %, or 1 wt. %, or as great as 3 wt. %, 4 wt. %, 5 wt. %, or 10 wt. %, or within any range defined between any two of the foregoing values, such as 0.3 to 10 wt. %, 0.3 to 5 wt. %, 0.5 to 4 wt. %, or 1 to 3 wt. %, for example, based on the total weight of the palladium catalyst and the aluminum support.

The alumina support may be alpha alumina ($\alpha$-$Al_2O_3$), beta alumina ($\beta$-$Al_2O_3$), or gamma alumina ($\gamma$-$Al_2O_3$), or a combination of the foregoing. As indicated in the Examples below, HCFO-1233xf is highly susceptible to the gas-phase hydrogenation catalyzed by palladium on an alumina support, with a conversion of HCFO-1233xf greater than 99.9% in some embodiments, with any concurrent hydrogenation of HCFC-244bb largely disfavored, typically less than 5%.

In addition to alumina supports, other catalyst supports such as carbon, alkaline earth carbonates, alkaline earth sulfates, silica, resin and graphite may also be used. Also, as an alternative to palladium, other metals, including nickel, platinum, rhenium, iron, ruthenium, and cobalt, may also be used with any of the above-mentioned catalyst supports.

The contact time between the HCFO-1233xf and HCFC-244bb reactant stream and the catalyst in reactor 12 may be as little as 5 seconds, 40 seconds, 50 seconds, or 1 minute, or as great as 90 seconds, 105 seconds, or 120 seconds, or within any range defined between any pair of the foregoing values, such as from 5 seconds to 120 seconds, from 50 seconds to 105 seconds, or from 1 minute to 90 seconds, for example.

Suitable reaction temperatures in reactor 12 may be as little as 100° C., 125° C., 150° C., or as great as 200° C., 225° C., or 250° C., or within any range defined between any pair of the foregoing values, such as from 100° C. to 250° C., from 125° C. to 225° C., or from 155° C. to 200° C., for example.

Suitable reaction pressures in reactor 12 may be as little as 5, psig, 20 psig, or 30 psig, or as great as 50 psig, 75 psig, or 100 psig, or within any range defined between any pair of the foregoing values, such as from 5 psig to 100 psig, from 20 psig to 75 psig, or from 30 psig to 50 psig, for example.

As shown below in Table 1, it has been found that the conversion of HCFO-1233xf is substantially independent of catalyst contact time, wherein the conversion remains substantially constant for the entire range of the catalyst contact time set forth in Table 1 below while, by contrast, conversion of HCFC-244bb increases with increasing catalyst contact time.

TABLE 1

Reactor space times and corresponding conversions of 244bb and 1233xf

| Feed rate (lb/hr) | Pressure (psig) | Temperature (° C.) | Space time (s) | Conversion 244bb (%) | Conversion 1233xf (%) |
|---|---|---|---|---|---|
| 0.3 | 50 | 190 | 117.92 | 0.62 | 99.44 |
| 0.6 | 60 | 198 | 68.06 | 0.39 | 99.20 |
| 1 | 60 | 198 | 40.83 | 0.27 | 98.40 |

In the present selective hydrogenation reaction, conversion of HCFO-1233xf may exceed 98%, 99% or, in some embodiments, even 99.9%, and conversion of HCFC-244bb may be minimized to less than 5%, less than 3% or, in some embodiments, less than 1%. The selectivity of HCFO-1233xf to HCFC-253db may exceed 30%, 50%, 60% or, in some embodiments, even 75%, The composition of the reactor effluent stream 16 from reactor 12 following the selective gas-phase hydrogenation of HCFO-1233xf to form HCFC-253db from a mixture of HCFO-1233xf and HCFC-244bb is shown below in Table 2.

TABLE 2

GC-MS peak report of reactor effluent for 1233xf hydrogenation over 0.5 wt % Pd/Al$_2$O$_3$, at 50 psig, 190° C. at 1.7 molar ratio of hydrogen

| Peak # | Retention time (min) | Component name | Area- FID | Area % FID |
|---|---|---|---|---|
| 1 | 10.617 | ethane | 859056 | 0.0037 |
| 2 | 10.809 | HFC-143a | 118551 | 0.0005 |
| 3 | 12.059 | HFC-245cb/-HFO-1234yf | 20301921 | 0.0879 |
| 4 | 13.04 | HFO-1243zf | 11156964 | 0.0483 |
| 5 | 13.55 | propane | 9154007 | 0.0396 |
| 6 | 14.386 | HFC-263fb | 1007736715 | 4.3633 |
| 7 | 14.694 | HFC-254eb | 18984889 | 0.0822 |
| 8 | 15.088 | HFC-245fa | 2102919 | 0.0091 |
| 9 | 15.656 | difluorodimethylsilane | 143110 | 0.0006 |
| 10 | 17.906 | HCFC-244bb | 21219655727 | 91.8776 |
| 11 | 18.666 | HCFC-244 isomer | 317186 | 0.0014 |
| 12 | 18.916 | HCFO-1233xf | 20947815 | 0.0907 |
| 13 | 19.118 | HCFO-1224 isomer | 454731 | 0.0020 |
| 14 | 20.185 | HCFC-253 isomer | 776258599 | 3.3611 |
| 15 | 20.368 | HCFC-253 isomer | 1334877 | 0.0058 |
| 16 | 20.974 | HCFC-244 isomer | 140284 | 0.0006 |
| 17 | 21.195 | HCFC-253 isomer | 3636879 | 0.0157 |
| 18 | 22.253 | unknown | 275137 | 0.0012 |
| 19 | 22.599 | unknown | 827085 | 0.0036 |
| 20 | 22.791 | hexafluoromethyl pentane isomer | 319314 | 0.0014 |
| 21 | 23.82 | HCFC-243db | 856147 | 0.0037 |

To promote optimum yield during the selective hydrogenation step, the reaction conditions set forth above are selected to minimize, or avoid, any reaction by HCFC-244bb. One feasible reaction pathway for HCFC-244bb is to undergo dehydrochlorination over the alumina support of the catalyst. Thermal dehydrochlorination of HCFC-244bb is also possible. Similarly, HCFC-253db, the immediate hydrogenation product of HCFO-1233xf, may also undergo dehydrochlorination to form 3, 3, 3-trifluoropropene (HFO-1243zf or 1243zf), which may also subsequently undergo hydrogenation to form 1, 1, 1 trifluoropropane (HFC-263fb or 263fb). Further, HCFC-244bb may undergo dehydrochlorination to form HFO-1234yf, which is then hydrogenated to form HFC-254eb. The presence of dehydrochlorination pathways, potentially catalyzed by the alumina catalyst support, may potentially lead to the thermal dehydrochlorination of HCFC-244bb and/or the potential formation of hydrochloric acid (HCl).

Still referring to FIG. 1, following the selective gas-phase hydrogenation of HCFO-1233xf from a mixture of HCFO-1233xf and HCFC-244bb, the reactor effluent stream 16 may then proceed to distillation column 18, where the effluent is distilled. A purified stream of HCFC-244bb (having a purity greater than 99.9%, for example) is removed from column 18 as overhead stream 20, while less volatile by-products are removed from column 18 as bottoms stream 22.

The HCFC-253db formed in the selective hydrogenation reaction has a higher boiling point relative to HCFO-1233xf and HCFC-244bb, and may be concentrated in a reboiler 24 associated with column 18 such that the HCFC-253db may be collected, removed, and further purified as desired in a separate product stream 26, with a recycle stream 28 returning to column 18 from reboiler 24. In particular, the HCFC-253db collected from reboiler 24 has application as a precursor for making monomers and other value-added refrigerants.

Secondary dehydrochlorination reactions in reactor 12 may result in the formation of HCl. However, it has been found that the overhead stream 20 from the distillation column 18 contains residual HCl in a minimized amount, such as less than 10 ppm, less than 5 ppm, or less than 1 ppm, for example.

The purified HCFC-244bb removed from column 18 as overhead stream 20 may proceed to an acid scrubber 30, for washing by a neutral or basic solution supplied to scrubber 30 via stream 32 in order to neutralize any acid, such as HCl, remaining in the purified HCFC-244bb overhead stream 20. One suitable base is a 10 pH solution of soda ash (Na$_2$CO$_3$) in water, though other bases may be used to form suitable basic solutions of varying pH greater than 7. For lower acid concentrations, water alone at substantially neutral pH may be supplied to scrubber 30.

The scrubbing may be accomplished in continuous or batch mode. For continuous scrubbing, a basic solution is continuously circulated through a packed column where the purified HCFC-244bb vapor is contacted to neutralize and remove acidic impurities. For a batch acid scrubbing system, a tank charged with a basic aqueous solution may be employed to remove the acidic impurities from a liquid purified HCFC-244bb batch.

In a still further embodiment, adsorbents such as carbon-based adsorbents, silica-based adsorbents, alumina-based adsorbents, microporous and mesoporous silica, metal organic frameworks and zeolites, may be used to remove any acid present in the distilled HCFC-244bb. This may be accomplished by continuously circulating the HCFC-244bb, in a vapor or liquid form, through a packed column containing one or a combination of the adsorbents listed above. The packed column containing one or more of the foregoing acid adsorbent(s) may also contain one or more water/moisture adsorbents, such as those set forth below, for moisture removal such that acid and moisture removal may be attained using the same packed column.

An agitator may be used in scrubber 30 to enhance contact between the HCFC-244bb and the basic wash solution and eventually, due to the higher density of the HCFC-244bb than the basic solution, the HCFC-244bb will separate as a bottom layer, and may be removed from scrubber 30 as stream 34, with used basic solution and water/moisture removed from scrubber 30 via stream 36 as needed.

The yield of the foregoing acid neutralization step, i.e., the purity of the HCFC-244bb following the drying step, is quantitative and specifically, may be greater than 99.9%, and the moisture and acidity content of the purified HCFC-244bb may be less than 10 ppm and less than 1.0 ppm, respectively. To ensure that HCFC-244bb remains in liquid form while being washed, at least 50 psig of a inert gas pad may be maintained in scrubber 30, and the temperature in scrubber 30 may be maintained below the boiling point of HCFC-244bb, namely, below 15° C. Maintaining HCFC-244bb in the liquid phase allows for desirable interaction with the basic wash solution and, when the contents of scrubber 30 are maintained at the reduced temperature specified above, facilitates phase separation of the contents of scrubber 30 by reducing the solubility of HCFC-244bb in the basic wash solution.

The acid-neutralized HCFC-244bb stream 34 may then proceed to drier 38, where any residual water/moisture is removed using a drying agent such as molecular sieves (zeolites), silica, anhydrous calcium sulfate ($CaSO_4$), sulfuric acid, anhydrous calcium chloride ($CaCl_2$), and activated charcoal. Preferably, the drying agent should be compatible with HCFC-244bb, chemically inert, and water-insoluble, to limit the introduction of impurities into the acid-neutralized HCFC-244bb.

The resultant purified HCFC-244bb stream 40 from drier 38 may be used as a reactant for Step 3 of the process described above for producing HFO-1234yf. The purified HCFC-244bb may have a purity greater than 95 wt. %, greater than 98 wt. %, or greater than 99.9 wt. %, may have an acid content of less than 1.0 ppm, 0.5 ppm, or less than 0.1 ppm, and may have a water (moisture) content of less than 10 ppm, less than 5 ppm, or less than 1 ppm.

Example 1

Selective Hydrogenation of HCFO-1233xf from a Mixture of HCFO-1233xf and HCFC-244bb, Using 0.5 wt. % $Pd/Al_2O_3$ A feed stream including HCFO-1233xf and 244bb was vaporized and reacted in the vapor phase over 0.5 wt. % $Pd/Al_2O_3$ to selectively hydrogenate HCFO-1233xf to make HCFC-253db. Specifically, the corresponding feed composition including HCFO-1233xf, HCFC-244bb, hydrogen, and other compounds was vaporized and fed to a 1" (2.54 cm) ID×31" (79 cm) L reactor containing 0.3 L of 0.5 wt. % $Pd/Al_2O_3$ pellets, at a rate ranging from 0.3-1 lb/hr (0.14-0.45 kg/hr), and a reactor pressure of 50 psig. The reaction temperature was varied from 190-200° C.

Typically, the conversion of HCFO-1233xf was quantitative (greater than 98%) while that of HCFC-244bb was less than 0.5%. The average productivity observed was 0.503 lb/hr/ft$^3$ (8.06 kg/hr/m$^3$). Table 3 below shows average conversions of HCFO-1233xf and HCFC-244bb, and average selectivity to HCFC-253db and by-products, as a function of temperature using 0.5 wt. % $Pd/Al_2O_3$ catalyst. The selectivity to HCFC-253db and 263fb originate from HCFO-1233xf, while the selectivity to HFC-254eb and HFO-1234yf originate from HCFC-244bb.

TABLE 3

Average conversions of HCFO-1233xf and HCFC-244bb during selective hydrogenation of HCFO-1233xf from a mixture of HCFO-1233xf and HCFC-244bb

| Temp., | Flow Rate, | Feed Composition | | | Average Conversion (%) | | Average Selectivity (%) | | | | |
| --- | --- | --- | --- | --- | --- | --- | --- | --- | --- | --- | --- |
| (° C.) | lb/hr | 1233xf | 244bb | Others | 1233xf | 244bb | 253db | 263fb | 254eb | 1234yf | Others |
| 190 | 0.3 | 6.905 | 93.08 | 0.015 | 99.26 | 0.39 | 54.89 | 44.01 | 88.81 | 11.19 | 1.10 |
| 200 | 0.6 | 1.203 | 98.436 | 0.36 | 99.34 | 0.14 | 40.72 | 32.49 | 92.70 | 7.30 | 26.79 |
| 200 | 1 | 1.203 | 98.436 | 0.36 | 98.45 | 0.35 | 33.67 | 37.36 | 84.38 | 15.62 | 28.97 |

Other conditions: catalyst: 0.5 wt. % $Pd/Al_2O_3$; reactor pressure: 50-60 psig; 0.3 L of catalyst; reactor dimensions: 1" ID × 31" L; mole ratio of hydrogen: 1.7: 1; each temperature was run for at least 30 h; average productivity: 0.503 lb/h/ft$^3$ (8.06 kg/hr/m$^3$)

Example 2

Selective Hydrogenation of HCFO-1233xf from a Mixture of HCFO-1233xf and HCFC-244bb A feed stream including HCFO-1233xf and 244bb was vaporized and reacted in the vapor phase over 0.5 wt. % $Pd/Al_2O_3$ to selectively hydrogenate HCFO-1233xf to make HCFC-253db. Specifically, the corresponding feed composition including HCFO-1233xf, HCFC-244bb, hydrogen, and other compounds was vaporized and fed to a 1" (2.54 cm) ID×31" (79 cm) L reactor containing 1.4 L of 0.5 wt. % $Pd/Al_2O_3$ pellets, at the corresponding feed rate, and reactor pressure of 50-70 psig. The reaction temperature was varied from 100-230° C.

Typically, the conversion of HCFO-1233xf was quantitative (greater than 99.9%) while that of HCFC-244bb was less than 0.5%. The average productivity observed was 18.85 lb/hr/ft$^3$ (301.95 kg/hr/m$^3$). Table 4 below shows average conversions of HCFO-1233xf and HCFC-244bb, and average selectivity to HCFC-253db and by-products, as a function of temperature using 0.5 wt. % Pd/Al₂O₃ catalyst. The selectivity to HCFC-253db and 263fb originate from HCFO-1233xf, while the selectivity to HFC-254eb and HFO-1234yf originate from HCFC-244bb.

through the soda ash solution, which favors the acid neutralization. The resultant solution in the 10 gallon (3.9 L) vessel was then agitated for 20-30 minutes, at 12 rpm. Upon mixing, the agitator was turned off and the mixture allowed to phase separate. HCFC-244bb has a boiling point of 15° C. To assure that it remained a liquid in the 10 gallon (3.9 L)

TABLE 4

Average conversions of HCFO-1233xf and HCFC-244bb during selective hydrogenation of HCFO-1233xf from a mixture of HCFO-1233xf and HCFC-244bb

| Temp. | Feed Composition, % | | | Average Conversion, % | | Average Selectivity, % | | | | |
|---|---|---|---|---|---|---|---|---|---|---|
| (° C.) | 1233xf | 244bb | others | 1233xf | 244bb | 253db | 263fb | 254eb | 1234yf | Others |
| 100 | 15.34 | 83.87 | 0.79 | >99.9 | 0 | 76.70 | 20.06 | 100.00 | 0.00 | 3.24 |
| 125 | 15.34 | 83.87 | 0.79 | >99.9 | 0 | 69.72 | 27.17 | 100.00 | 0.00 | 3.11 |
| 150 | 15.34 | 83.87 | 0.79 | >99.9 | 2.46 | 54.97 | 43.95 | 73.92 | 26.08 | 1.08 |
| 175 | 15.34 | 83.87 | 0.79 | >99.9 | 2.73 | 53.27 | 40.20 | 100.00 | 0.00 | 6.53 |
| 200 | 4.20 | 95.33 | 0.47 | >99.9 | 1.34 | 31.58 | 67.69 | 11.71 | 88.29 | 0.73 |
| 200 | 7.80 | 92.03 | 0.17 | >99.9 | 1.76 | 47.58 | 46.65 | 70.09 | 29.91 | 5.76 |
| 200 | 9.50 | 89.23 | 1.26 | >99.9 | 1.02 | 48.75 | 50.55 | 16.04 | 83.96 | 0.70 |
| 230 | 9.50 | 89.23 | 1.26 | >99.9 | 3.12 | 40.60 | 58.52 | 17.24 | 82.76 | 0.88 |

Other conditions: catalyst: 0.5 wt % Pd/Al2O3; 1.4 L of catalyst; flow rate: 2.5 lb/h; reactor pressure: 50-70 psig; reactor dimensions: 2" ID x 31" L; mole ration of hydrogen: 1.7: 1; each temperature was run for at least 10 h, average productivity: 18.85 lb/h/ft³ (301.95 kg/hr/m³)

Example 3

Distillation of the product from the selective hydrogenation of HCFO-1233xf from a mixture of HCFO-1233xf and HCFC-244bb The reactor effluent stream from the selective hydrogenation of HCFO-1233xf from a mixture of HCFO-1233xf and HCFC-244bb, to form HCFC-253db (Examples 1 and 2 above) was consolidated and distilled to afford a pure stream of HCFC-244bb (greater than 99.9 wt. % purity). The composition of the reactor effluent stream consisted mostly of HCFO-1233xf, HCFC-244bb, HFO-1234yf, HFC-263fb, HFC-254eb, HFO-1243zf, HCFC-253db and other compounds. To the reboiler of the distillation column was charged 100 lb (45.4 kg) of material with the aforementioned composition. The pressure of the column ranged from 20-30 psig, while the temperature ranged from 30-40° C. The d/p ranged from 10-20 in H₂O. The takeoff rate ranged from 0.5-3 lb/hr (0.23-1.36 kg/hr). Volatile components such as HFO-1234yf, HFC-263fb, HFO-1243zf, and HFC-254eb were removed through the overhead stream, followed by the HCFC-244bb product, while HCFC-253db was concentrated in the reboiler. After distilling about 2000 lb (907 kg) of material from the reactor effluent, about 100 lb (45.4 kg) of HCFC-253db were collected from the reboiler. The purity of HCFC-244bb was greater than 99.9% and the yield of the distillation ranged from 90-95%.

Example 4

Batch Acid Neutralization with 10 pH Solution of Soda Ash in Water, Followed by Drying The acid neutralization step was conducted using a 10 gallon (3.9 L) vessel equipped with an agitator. All distilled HCFC-244bb, at 99.9+% purity and <10 ppm acidity, was washed using a 10 pH solution of soda ash in water (Na₂CO₃/H₂O). The wash procedure entailed charging 15 lb (6.8 kg) of the 10 pH soda ash solution into the 10 gallon (3.9 L) vessel, followed by 50 lb (22.7 kg) of HCFC-244bb. This addition sequence allows HCFC-244bb to sieve through the soda ash solution, which favors the acid neutralization. The resultant solution in the 10 gallon (3.9 L) vessel was then agitated for 20-30 minutes, at 12 rpm. Upon mixing, the agitator was turned off and the mixture allowed to phase separate. HCFC-244bb has a boiling point of 15° C. To assure that it remained a liquid in the 10 gallon (3.9 L) vessel, 50 psig of nitrogen gas pad was maintained in the vessel, with chilled ethylene glycol, at −5° C., continuously being circulated in the jacket of the vessel. Maintaining HCFC-244bb in the liquid phase allows for optimal interaction with the soda ash solution, and circulating chilled coolant in the jacket keeps the content of the vessel cool, which facilitates phase separation as it reduces the solubility of HCFC-244bb in the 10 pH solution of soda ash in water.

Following phase separation, HCFC-244bb, which is denser than the soda ash solution, forms the organic phase below the soda ash solution. This aspect was used to advantage as multiple batches of HCFC-244bb were washed without changing the soda ash solution. Specifically, 20 batches of HCFC-244bb (50 lb (22.7 kg) per batch and total amount of 1000 lb (453.6 kg)) were washed using 15 lb (6.8 kg) of 10 pH solution of soda ash in water. The organic phase, which was HCFC-244bb, was drained from 10 gallon (3.9 L) vessel through dryers, containing Drierite, en route to a final product collection cylinder. The acid concentration and moisture concentration of the HCFC-244bb in the product collection cylinder were routinely analyzed. The concentration of moisture and acidity of the cumulative washed HCFC-244bb were <5 ppm and <1 ppm, respectively.

While this disclosure has been described as relative to exemplary designs, the present disclosure may be further modified within the spirit and scope of this disclosure. Further, this application is intended to cover such departures from the present disclosure as come within known or customary practice in the art to which this disclosure pertains.

The invention claimed is:

1. A method for producing 2-chloro-1,1,1,2-tetrafluoropropane (HCFC-244bb), comprising the steps of:
   providing a reactant stream including a mixture of HCFC-244bb and 2-chloro-3,3,3-trifluoropropene (HCFO-1233xf), the amount of HCFO-1233xf between 5 wt. % and 25 wt. % based on a total weight of the reactant stream; and
   hydrogenating the HCFO-1233xf of the reactant stream in a vapor phase in the presence of hydrogen gas and a palladium catalyst diluted in an alpha aluminum support to a palladium loading between 0.3 wt. % and 0.5 wt. %, based on the total weight of the palladium catalyst and the alpha aluminum support, to generate a product composition including unreacted HCFC-244bb and 2-chloro-1,1,1-trifluoropropane (HCFC-253db).

2. The method of claim 1, wherein the reactant stream includes between 75 wt. % and 98 wt. % HCFC-244bb, based on the total weight of the reactant stream.

3. The method of claim 1, wherein the hydrogenation step further comprises hydrogenating at a temperature between 100° C. and 250° C.

4. The method of claim 1, wherein the hydrogenation step further comprises hydrogenating at a pressure between 5 psig and 100 psig.

5. The method of claim 1, further comprising the additional step of separating the HCFC-244bb and the HCFC-253db.

6. The method of claim 5, further comprising the additional steps of:
    subjecting the separated HCFC-244bb to an acid neutralization step; and
    drying the acid neutralized HCFC-244bb.

7. The method of claim 6, wherein, following the drying step, the HCFC-244bb has at least one of:
    a purity greater than 95 wt. %;
    a water content less than 10 ppm; and
    an acid content less than 1 ppm.

8. The method of claim 1, wherein, in the hydrogenating step, conversion of HCFO-1233xf exceeds 98%.

9. The method of claim 1, wherein, in the hydrogenating step, selectivity of HCFO-1233xf to HCFC-253db exceeds 60%.

10. A method for producing 2-chloro-1,1,1,2-tetrafluoropropane (HCFC-244bb), comprising the steps of:
    providing a reactant stream including a mixture of HCFC-244bb and 2-chloro-3,3,3-trifluoropropene (HCFO-1233xf), the amount of HCFO-1233xf between 5 wt. % and 25 wt. % based on a total weight of the reactant stream;
    hydrogenating the HCFO-1233xf of the reactant stream in a vapor phase in the presence of hydrogen gas and a palladium metal catalyst diluted in an alpha aluminum support to a palladium loading between 0.3 wt. % and 0.5 wt. %, based on the total weight of the palladium catalyst and the alpha aluminum support, at a temperature between 100° C. and 250° C. to generate a product composition including unreacted HCFC-244bb and 2-chloro-1,1,1-trifluoropropane (HCFC-253db); and
    separating the HCFC-244bb and the HCFC-253db.

11. The method of claim 10, further comprising the additional steps of:
    subjecting the separated HCFC-244bb to an acid neutralization step; and
    drying the acid neutralized HCFC-244bb.

12. The method of claim 11, wherein, following the drying step, the HCFC-244bb has a purity greater than 95 wt. %, a water content less than 10 ppm, and an acid content less than 1 ppm.

13. The method of claim 10, wherein the reactant stream includes between 75 wt. % and 98 wt. % HCFC-244bb, based on the total weight of the reactant stream.

14. The method of claim 10, wherein the hydrogenation step further comprises hydrogenating at a pressure between 5 psig and 100 psig.

15. The method of claim 10, wherein, in the hydrogenating step, conversion of HCFO-1233xf exceeds 98%.

16. The method of claim 1, wherein, in the providing step, the reactant stream is diluted by an inert diluent, the inert diluent present in the reactant stream in an amount between 2 wt. % and 25 wt. %, based on the total weight of the HCFO-1233xf and the HCFC-244bb in the reactant stream.

17. The method of claim 1, wherein, in the hydrogenating step, the hydrogen gas is diluted by an inert diluent, the inert diluent present in the hydrogen gas in an amount between 2 wt. % and 40 wt. %, based on a total weight of the hydrogen gas.

18. The method of claim 10, wherein, in the providing step, the reactant stream is diluted by an inert diluent, the inert diluent present in the reactant stream in an amount between 2 wt. % and 25 wt. %, based on the total weight of the HCFO-1233xf and the HCFC-244bb in the reactant stream.

19. The method of claim 10, wherein, in the hydrogenating step, the hydrogen gas is diluted by an inert diluent, the inert diluent present in the hydrogen gas in an amount between 2 wt. % and 40 wt. %, based on a total weight of the hydrogen gas.

* * * * *